US012394521B2

(12) United States Patent
Pasternak et al.

(10) Patent No.: US 12,394,521 B2
(45) Date of Patent: Aug. 19, 2025

(54) SLEEP APNEA TEST DEVICE

(71) Applicant: Itamar Medical Ltd., Caesarea (IL)

(72) Inventors: Michael Pasternak, Bat Yam (IL); Itay Kariv, Haifa (IL); Rafi Koby, Kochav Yair (IL)

(73) Assignee: Itamar Medical Ltd., Caesarea (IL)

( * ) Notice: Subject to any disclaimer, the term of this patent is extended or adjusted under 35 U.S.C. 154(b) by 680 days.

(21) Appl. No.: 17/215,545

(22) Filed: Mar. 29, 2021

(65) Prior Publication Data

US 2022/0148724 A1  May 12, 2022

Related U.S. Application Data

(60) Provisional application No. 63/112,418, filed on Nov. 11, 2020.

(51) Int. Cl.
*G16H 40/67* (2018.01)
*A61B 5/00* (2006.01)
(Continued)

(52) U.S. Cl.
CPC ............ *G16H 40/67* (2018.01); *A61B 5/0022* (2013.01); *A61B 5/0024* (2013.01); *A61B 5/4818* (2013.01); *A61B 5/681* (2013.01); *G16H 10/60* (2018.01); *A61B 5/1118* (2013.01); *A61B 5/6823* (2013.01); *A61B 5/6826* (2013.01); *A61B 2505/07* (2013.01); *A61B 2560/0214* (2013.01); *A61B 2560/0475* (2013.01); *A61B 2562/08* (2013.01)

(58) Field of Classification Search
None
See application file for complete search history.

(56) References Cited

U.S. PATENT DOCUMENTS 7,621,877 B2  11/2009  Schnall
7,806,831 B2  10/2010  Lavie et al.
(Continued)

FOREIGN PATENT DOCUMENTS

WO   WO-2004100034 A1 *  11/2004  ........... A61B 5/0002
WO   WO-2021067767 A1 *   4/2021  ......... A61B 5/14532

OTHER PUBLICATIONS

Wu et al., Access Control Schemes for Implantable Medical Devices: A Survey, IEEE Internet of Things Journal, vol. 4, No. 5, Oct. 2017, pp. 1272-1283 (Year: 2017).*

(Continued)

*Primary Examiner* — Anne-Marie K Alderson
(74) *Attorney, Agent, or Firm* — The Webb Law Firm

(57) ABSTRACT

Systems and methods for securely transferring medical data for an off-site administered test. A method includes receiving, at a first device, a key associated with a second device from a third device, wherein the second device is a medical device having a unique identifier, wherein the second device includes at least one sensor configured to capture medical data; receiving, at the first device, a request to store the medical data captured by the at least one sensor from the second device; configuring the second device to store the medical data in at least one designated storage location, wherein each designated storage location is accessible to the second device and to the third device; and sending the designated storage location and the unique identifier to the third device.

13 Claims, 15 Drawing Sheets

(51) Int. Cl.
*A61B 5/11* (2006.01)
*G16H 10/60* (2018.01)

(56) References Cited

U.S. PATENT DOCUMENTS

| | | | | |
|---|---|---|---|---|
| 8,821,418 B2* | 9/2014 | Meger | ............... | A61B 5/02055 600/595 |
| 9,009,437 B1* | 4/2015 | Bjornsson | ............ | G06F 3/0641 718/1 |
| 11,011,271 B2* | 5/2021 | Boucher | ................. | A61B 7/04 |
| 11,202,603 B1* | 12/2021 | Frederick | ............. | A61B 5/4815 |
| 2002/0013519 A1* | 1/2002 | Adams | .................. | G16H 40/67 600/300 |
| 2005/0192837 A1* | 9/2005 | Fears | .................... | G06Q 10/10 705/2 |
| 2007/0239055 A1* | 10/2007 | Sowelam | ............... | G16H 40/63 600/529 |
| 2007/0271316 A1* | 11/2007 | Hollebeek | ............ | G16H 30/20 |
| 2008/0319277 A1* | 12/2008 | Bradley | ................ | A61B 7/003 600/301 |
| 2009/0203970 A1* | 8/2009 | Fukushima | .......... | A61B 5/0205 600/301 |
| 2011/0046498 A1* | 2/2011 | Klap | .................... | A61B 5/0205 600/534 |
| 2011/0093284 A1* | 4/2011 | Dicks | .................... | G16H 40/67 705/2 |
| 2012/0247472 A1* | 10/2012 | Lynch, Jr. | ......... | A61M 16/0051 128/204.23 |
| 2014/0257833 A1* | 9/2014 | Williams | ............... | G16H 40/40 705/2 |
| 2015/0164410 A1* | 6/2015 | Selvaraj | ................. | A61B 5/316 600/509 |
| 2015/0305675 A1* | 10/2015 | Miller | ................... | G16H 40/67 600/301 |
| 2018/0014779 A1* | 1/2018 | Donnelly | ................. | A61N 1/39 |
| 2018/0176019 A1* | 6/2018 | Lee | ....................... | H04L 67/306 |
| 2019/0000375 A1* | 1/2019 | Ferreira Dos Santos Da Fonseca | .................... | A61B 5/11 |
| 2019/0365315 A1* | 12/2019 | Ramabadran | .......... | A61B 5/087 |
| 2020/0015737 A1 | 1/2020 | Pee et al. | | |
| 2020/0197681 A1* | 6/2020 | Bodnicki | ........... | A61M 39/0208 |
| 2020/0227160 A1* | 7/2020 | Youngblood | ........... | G16H 50/20 |
| 2020/0252436 A1* | 8/2020 | Yoon | ................. | H04W 52/0229 |
| 2020/0330030 A1* | 10/2020 | Fu | ....................... | A61B 5/0205 |

OTHER PUBLICATIONS

What to Know About an At-Home Sleep Test, www.hopkinsmedicine.org, accessed via WayBack machine Oct. 23, 2020. (Year: 2020).*

* cited by examiner

SLEEP APNEA TEST DEVICE

CROSS-REFERENCE TO RELATED APPLICATIONS

This application claims the benefit of U.S. Provisional Application No. 63/112,418 filed on Nov. 11, 2020, the contents of which are hereby incorporated by reference.

All of the applications referenced above are hereby incorporated by reference.

TECHNICAL FIELD

The present disclosure relates generally to home sleep apnea testing, and more specifically to single-use units for performing home sleep apnea tests.

BACKGROUND

Sleep apnea is a sleep disorder in which breathing pauses or is shallow more often than normal during sleep. Sleep apnea affects normal sleep and, therefore, may cause affected individuals to feel sleepiness or tiredness during the day. Diagnosing an individual with sleep apnea can lead to treatment which will improve the individual's quality of life.

Historically, sleep apnea was diagnosed by a medical professional observing sleep. Although this may be somewhat effective, it is inconvenient for a patient. Some home tests have been developed. In particular, oximetry may be performed noninvasively by monitoring the patient's oxygen saturation using a sensor device. As a result, oximetry may be tested in the comfort of a patient's home. Although more convenient than alternatives requiring manual observation, the test itself is less reliable.

It would therefore be advantageous to provide a solution that would provide a new and more reliable home testing for sleep apnea.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include a method for securely transferring medical data for an off-site administered test. The method comprises: receiving, at a first device, a key associated with a second device from a third device, wherein the second device is a medical device having a unique identifier, wherein the second device includes at least one sensor configured to capture medical data; receiving, at the first device, a request to store the medical data captured by the at least one sensor from the second device; configuring the second device to store the medical data in at least one designated storage location, wherein each designated storage location is accessible to the second device and to the second device and to the third device; and sending the designated storage location and the unique identifier to the third device.

Certain embodiments disclosed herein also include a non-transitory computer readable medium having stored thereon causing a processing circuitry to execute a process, the process comprising: receiving, at a first device, a key associated with a second device from a third device, wherein the second device is a medical device having a unique identifier, wherein the second device includes at least one sensor configured to capture medical data; receiving, at the first device, a request to store the medical data captured by the at least one sensor from the second device; configuring the second device to store the medical data in at least one designated storage location, wherein each designated storage location is accessible to the second device and to the third device; and sending the designated storage location and the unique identifier to the third device.

Certain embodiments disclosed herein also include a system for securely transferring medical data for an off-site administered test. The system comprises: a processing circuitry; and a memory, the memory containing instructions that, when executed by the processing circuitry, configure the system to: receive, at a first device, a key associated with a second device from a third device, wherein the second device is a medical device having a unique identifier, wherein the second device includes at least one sensor configured to capture medical data; receive, at the first device, a request to store the medical data captured by the at least one sensor from the second device; configure the second device to store the medical data in at least one designated storage location, wherein each designated storage location is accessible to the second device and to the third device; and send the designated storage location and the unique identifier to the third device.

Certain embodiments disclosed herein also include a home sleep apnea test device. The home sleep apnea test device comprises: a housing, the housing including a top portion and a bottom portion; wherein the top portion includes an electronic circuit placer, a battery compartment, a plurality of guide pins, a plurality of cross pins, and a plurality of loops; wherein the bottom portion includes a first plurality of anchor points adapted to accept respective guide pins of the plurality of guide pints, a second plurality of anchor points adapted to accept respective cross pins of the plurality of cross pins, a plurality of hooks adapted to connect to respective loops of the plurality of loops, an opening disposed opposite to the battery compartment for inserting a battery, a first channel, a second channel, a first edge, and a second edge that is parallel to the first edge; wherein the first channel is disposed on the first edge; wherein the second channel is disposed on the second edge; wherein each of the first channel and the second channel defines a respective perforation; a first band, the first band including a first end and a second end, the first band further including a buckle disposed at the first end and a wide portion at the second end, wherein the wide portion defines a perforation through which one of the plurality of cross pins is disposed, wherein the wide portion is secured by one of the plurality of second anchor points; a second band, the second band including a plurality of adjustment holes and a wide portion for being disposed in the second channel, the wide portion defining a perforation through which one of the plurality of cross pins is disposed, wherein the wide portion is secured by one of the plurality of second anchor points; a circuit board having a control circuit, wherein the control circuit is communicatively connected to an actigraph and the finger probe, wherein the circuit board is disposed on the electronic circuit placer.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1A:
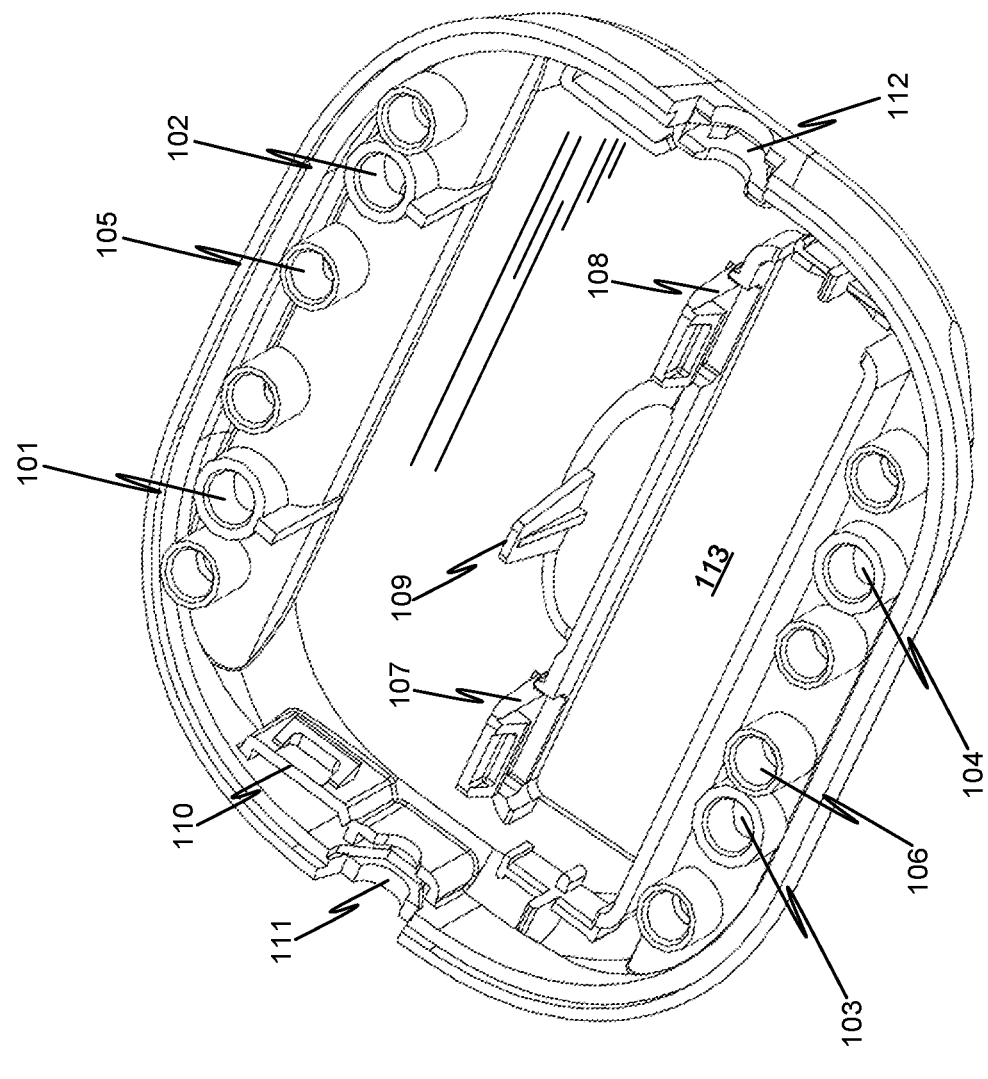
FIG. 1A is an internal facing isometric schematic illustration of a bottom portion of an HSAT device housing according to an embodiment.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

The various disclosed embodiments include a sleep apnea test device which allows for convenient home use by patients. The test device includes a housing having a top portion and a bottom portion, a first band having a buckle at a distal end and a wide portion at an end opposite the distal end, a second band having a plurality of adjustment holes and a wide portion, a control circuit, and a housing unit.

The top portion of the housing includes an electronic circuit placer, a battery compartment, guide pins, cross pins, and loops. The bottom portion of the housing includes a first set of anchor points for accepting the guide pins, a second set of anchor points for accepting the cross pins, a set of hooks, an opening for inserting a battery into the housing, a first channel, and a second channel. Each hook is for connecting to a loop.

The various disclosed embodiments also include a method for securely transferring data from an off-site administered test. A key associated with a medical device is received from an administrator device. A request to store data generated by one or more sensors of the medical device is received from the medical device. The medical device is reconfigured to store the data at a designated storage location accessible to the medical device over one or more networks. Data indicating the designated storage location and the unique identifier of the medical device is sent to the administrator device.

Figure 1B:
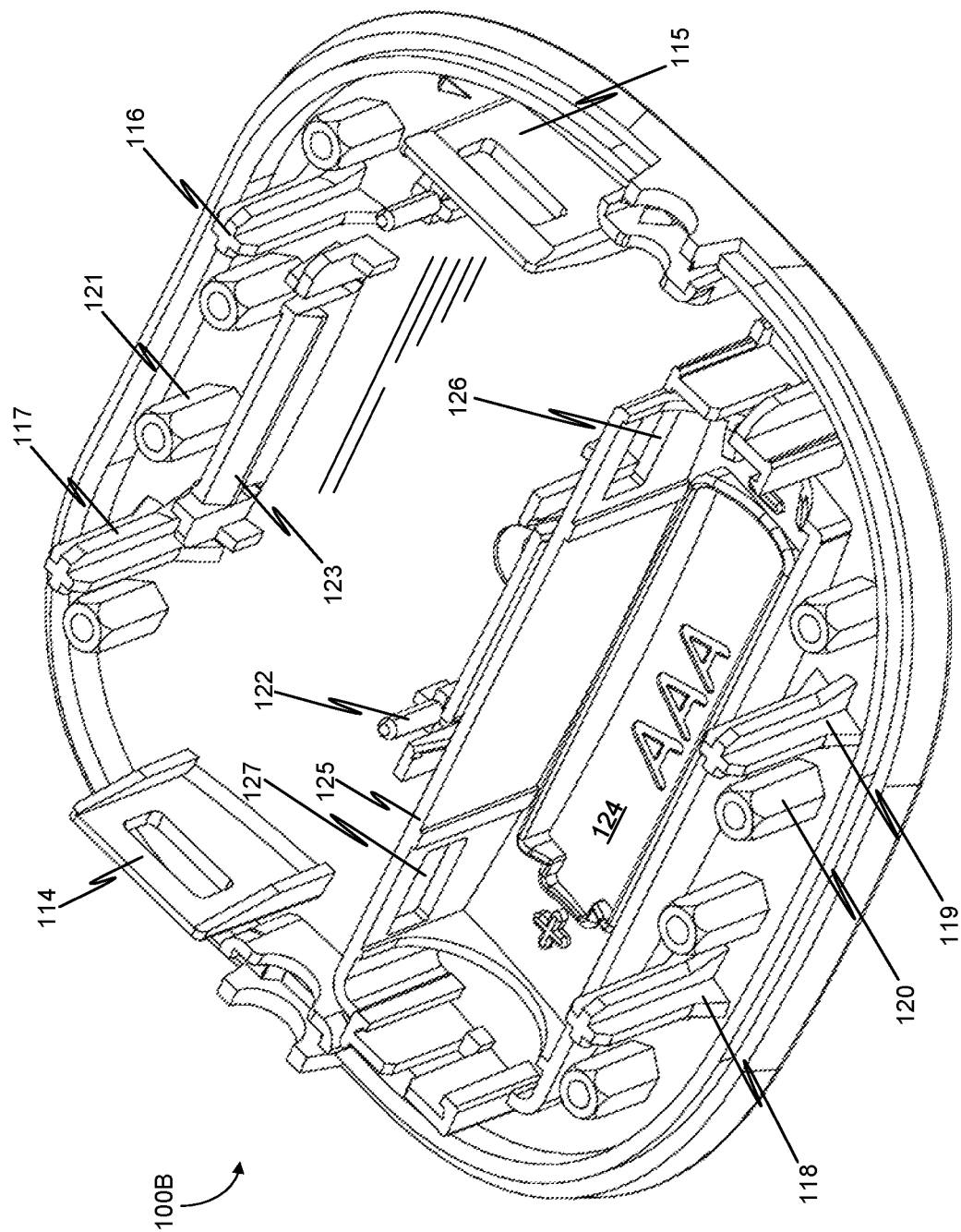
FIG. 1B is an internal facing isometric schematic illustration of a top portion of an HSAT device housing according to an embodiment.

FIG. 1A is an internal facing isometric schematic illustration of a bottom portion 100A of a home sleep apnea testing (HSAT) device housing according to an embodiment. FIG. 1B is an internal facing isometric schematic illustration of a top portion 100B of a HSAT device housing according to an embodiment.

An HSAT device housing includes a bottom portion 100A and a top portion 100B which interlock together to form the HSAT device housing. The bottom portion 100A includes a first anchor point 101, a second anchor point 102, a third anchor point 103 and a fourth anchor point 104. The anchor points 101 through 104 make up a collective well into which an anchor may be positioned. In an embodiment, the bottom portion 100A may further include one or more guide anchor points such as guide anchor points 105 and 106, which provide further support when connecting the top portion 100B to the bottom portion 100A.

The guide anchor points 105 and 106 may be positioned in a pattern such that joining of the top portion 100B to the bottom portion 100A is possible only in a single combined orientation of the top portion 100B and of the bottom portion 100A. It should be readily understood that a pair consisting of an anchor point and guide pin may be utilized such that each may be either on the top portion or bottom portion of the housing. In some embodiments, one or more guide pins may be disposed on the top portion (with corresponding anchor points disposed on the bottom portion) and one or more guide pins may be disposed on the bottom portion (with corresponding anchor point on the top portion).

The bottom portion 100A further includes a cavity 113 through which an energy source, such as a battery, may be inserted into the HSAT device housing once it is assembled. The cavity 113 is defined by a perforation on one side and a compartment on an opposing side. One or more hooks such as hooks 107, 108, and hook 110 which is orthogonal to hooks 107 and 108, may be disposed on the bottom portion 100A. The hooks 107, 108, and 110 are operative for attaching each to a corresponding loop of the top portion 100B. Once the HSAT device housing is assembled and the hooks 107, 108, and 110 are attached to corresponding loops (e.g., the loops 126, 127, and 114, respectively), opening the housing without damaging it is difficult due to the combination of hooks and loops which are orthogonal to each other.

Applying force in one direction to release a first hook and loop does not cause the housing to open, since at least one other hook and loop positioned orthogonally would not be affected by the applied force. It is advantageous to have a housing which is tamper resistant, as it is not advisable to tamper with a medical device. A housing which is tamper resistant without requiring additional fasteners, such as screws, is cheaper to manufacture, and therefore increases the affordability of the device. The disclosed embodiments allow for such tamper-resistance without requiring fasteners at least due to the hook and loop combinations, at least some of which are orthogonal to each other.

In an embodiment, the hooks may be implemented as cantilever snap fits with corresponding loops implemented as holes or recesses. It should be readily understood that pairs of hooks and loops may be implemented such that one or more hooks are on the top portion (with corresponding loops on the bottom portion) and one or more hooks are on the bottom portion (with corresponding loops on the top portion).

A pressure pin 109 protrudes orthogonally from the inner surface to hold a circuit board (not shown) in place. The pressure pin 109 applies pressure on the circuit board which is positioned on the top portion as shown in FIG. 1B. A perimeter of the bottom portion 100A has inclusions 111 and 112 which allow connector cable to pass through to a control circuit housed in the HSAT device housing.

Reference is now made to FIG. 1B. A loop 114 connects to the hook 110 as shown in FIG. 1A, and the loop 115 connects to a corresponding hook of the bottom portion 100A (not shown). Loop 126 which is orthogonal to loop 114 connects to hook 107 of bottom portion 100A, and loop 127 which is also orthogonal to loop 114 (and colinear to loop 126) connects to hook 108 as shown in FIG. 1A. Guide pin 120 connects to the guide anchor point 106 as shown in FIG. 1A, and guide pin 121 connects to the guide anchor point 105 as shown in FIG. 1A.

A plurality of cross pins 116 through 119 protrude from the inner surface of the top portion 100B. In this embodiment, cross pin 116 connects to anchor point 101, cross pin 117 connects to anchor point 102, cross pin 118 connects to anchor point 104, and cross pin 119 connects to anchor point 103. Connecting the cross pins 116 through 119 to the anchor points 101 through 104 is part of the mechanism connecting the HSAT device housing components together, and also serves to connects straps (also referred to as bands, not shown in FIGS. 1A-B) to the housing, as described in more detail below.

From the inner surface of the top portion 100B may further protrude a plurality of supports, such as support 122. A support is operative for securing in place a circuit board, such as a printed circuit board. For example, a support may be tapered such that the bottom portion (which is disposed closer to the inner surface of the top portion 100B) of the support is wider than a top portion. A printed circuit board (PCB, not shown) may have a corresponding perforation with a diameter larger than the top portion of the support and smaller than the bottom portion of the support. Multiple supports and corresponding perforations may be used to situate the PCB. A PCB may be further held in place by one or more hooks, such as hook 123. As the PCB is pushed towards the inner surface of the top portion 100B, the growing diameter of the supports exerts a force in the opposite direction. By placing the PCB such that the hook 123 further holds it in tension, the PCB is secured in its place. Securing the PCB using this structure and method do not require fasteners or adhesives which, if used, would increase the product's bill of materials (BoM) cost and could have other deficiencies, such as loosening up over time. Thus, the housing is cheaper to construct in terms of material and labor cost, which is advantageous for the manufacturer.

A battery compartment 124 is opposite to the cavity 113 of FIG. 1A. The battery compartment is defined by at least one wall 125 which is orthogonal to the inner surface of the top portion 100B. The wall 125 defines a first perforation 126 and a second perforation 127 which serve as loops for hooks 107 and 108, respectively.

Figure 1C:
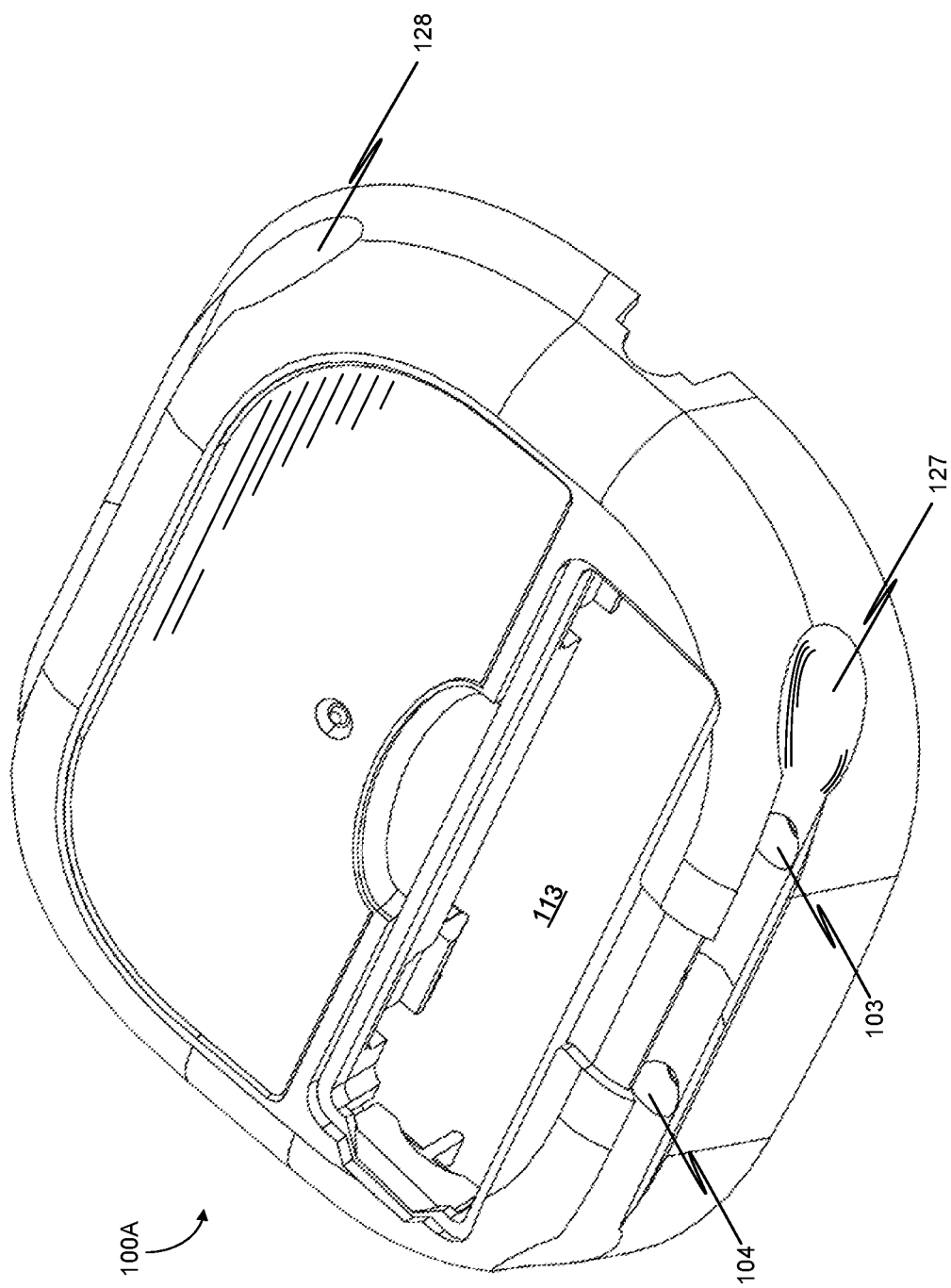
FIG. 1C is an external facing isometric schematic illustration of the bottom portion of an HSAT device housing according to an embodiment.

FIG. 1C is an external facing isometric schematic illustration of the bottom portion 100A of the HSAT device housing according to an embodiment. The bottom portion of the HSAT device housing further includes a first channel 127 and a second channel 128. The channels 127 and 128 are at least partially perforated such that the first channel 127 is perforated by the third anchor point 103 and the fourth anchor point 104. When the cross pin 118 is placed through the first channel 127 to connect to anchor point 104, and cross pin 119 is placed through the first channel 127 to connect to anchor point 103, the cross pins 118 and 119 pass through a band (not shown) having a member which corresponds in shape to the channel, thereby securing the band in place to the housing. Typically, securing a band to a housing is done with a hinge mechanism, such as is common for wrist watches. The disclosed embodiments, however, do not require a hinge, and may therefore be less costly to produce and is easier to assemble than mechanisms which require a hinge.

Figure 2A:
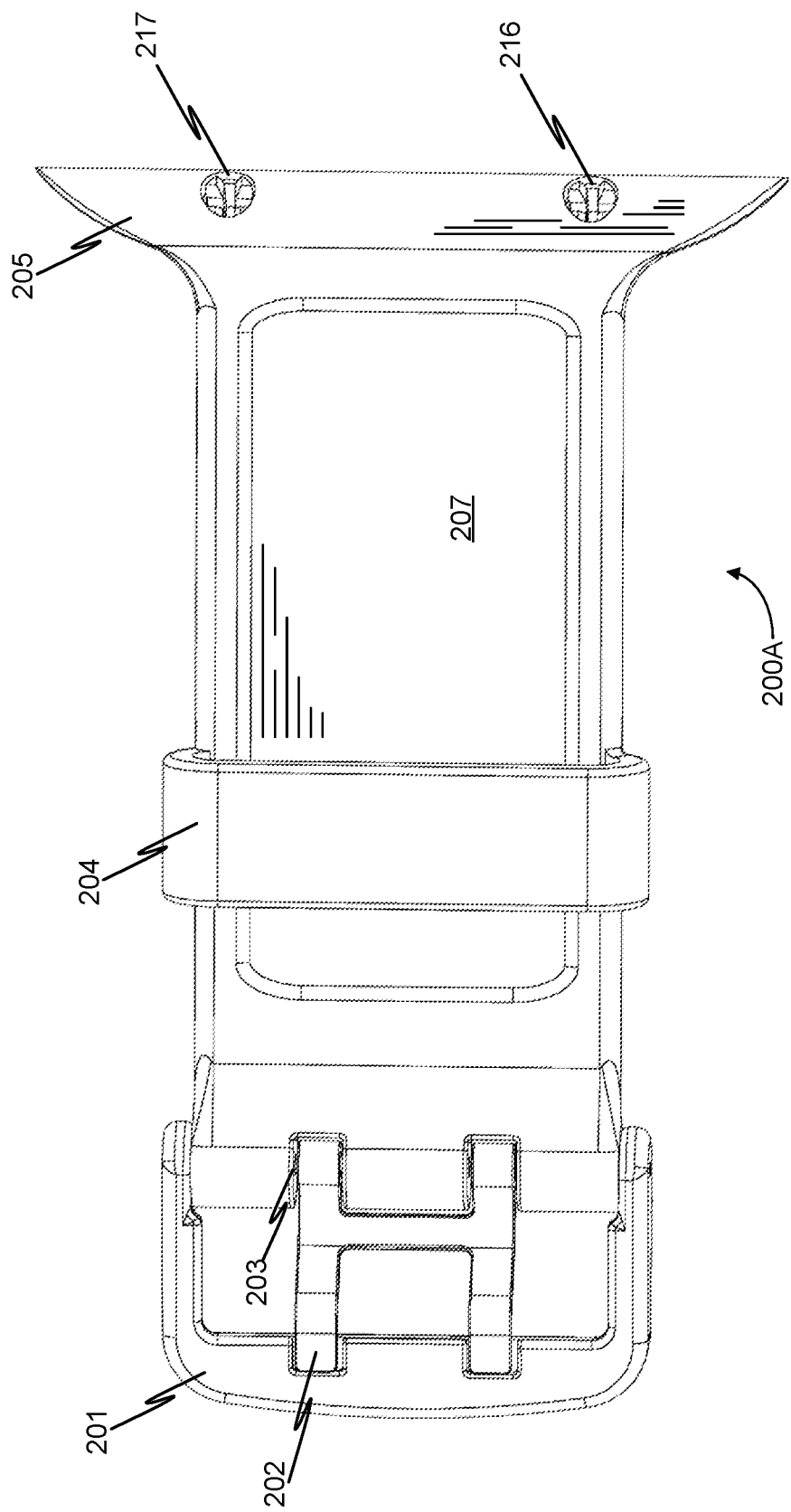
FIG. 2A is a schematic illustration of a top view of a buckle clasp band according to an embodiment.
Figure 2B:
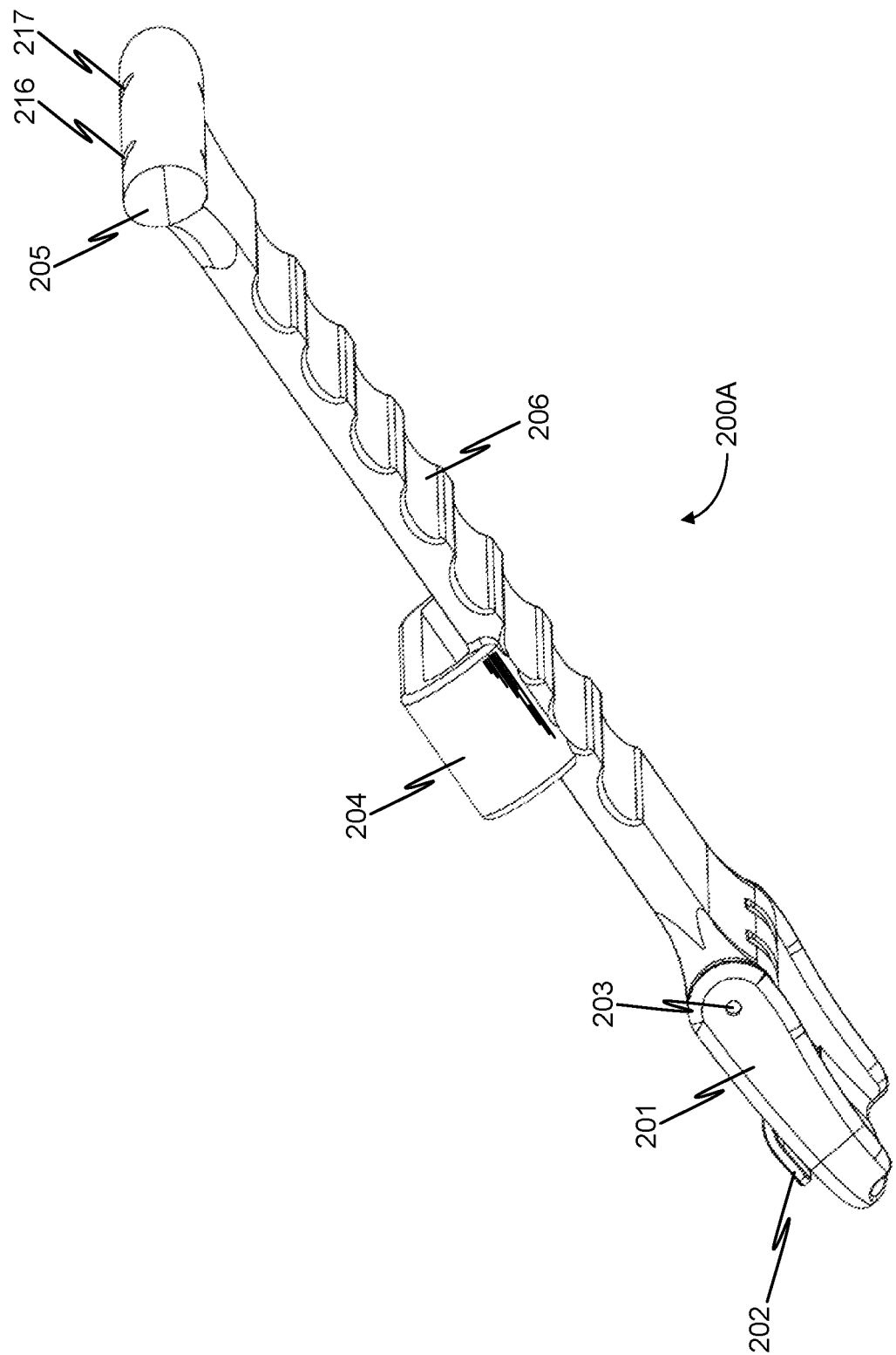
FIG. 2B is an isometric illustration of a bottom right view of the buckle clasp band according to an embodiment.

FIG. 2A is a schematic illustration of a top view of a buckle clasp band 200A according to an embodiment. FIG. 2B is an isometric illustration of a bottom right view of the buckle clasp band 200A according to an embodiment. The buckle clasp band 200A is operative together with a perforated band (e.g., the perforated band 300A discussed in more detail below) to form a fastening mechanism for fastening a HSAT device housing (e.g., the housing formed by the bottom and top portions 100A and 100B) to an appendage of a human subject such as a finger, arm, or leg.

The buckle clasp band 200A includes a fastening mechanism, such as a buckle frame 201 and a prong 202 which are attached to a band 207 via a hinge 203. The band 207 may be fabricated from a flexible material such as, but not limited to, textile, plastic, silicon rubber, or leather. In an embodiment the band 207 may further include a guide 204 which holds a perforated band (e.g., the perforated band 300A, FIG. 3A) in place once it has been clasped with the buckle and passed through the guide 204.

The buckle clasp band 200A tapers wider at an end 205 opposite to the fastening mechanism formed by the frame 201 and prong 202. The wide end 205 includes a first perforation 217 and a second perforation 216. The member 205 is fitted into channel 128 of the bottom portion 100A so that first perforation 217 is position aligned with anchor point 102 and second perforation 216 is aligned with anchor point 101 of the bottom portion 100A. When the two housing portions 100A and 100B are assembled, the cross pin 117 protrudes through the first perforation 217 and is held in position at anchor point 102, and the cross pin 116 protrudes through the second perforation 216 and is held in position at anchor point 101. In an embodiment, the distance between anchor points 101 and 102 is larger (or smaller) than the distance between anchor points 103 and 104. By implementing different distances between pairs of anchor points, it can be ensured that the bands are affixed in a single correct position, thereby ensuring the quality of assembly.

As shown in FIG. 2B, in an embodiment, the buckle clasp band 200A may further include a plurality of ridges such as the ridges 206. Ridge structure adds flexibility to the band, making it less rigid. Another advantage of the ridge structure is to prevent occlusion of blood flow to and from the appendage. Blood flow to the test site and in general to any extremity of the human body might alter the test results (such as by affecting oxygenation values) or cause physiological harm. Thus, a ridge structure such as the ridge 206 may be utilized in some embodiments to avoid these issues. In some embodiments (not shown), a plurality of concavities or a combination of concavities and ridges may be utilized.

The test site may be, for example, a finger. A finger probe may be placed on a distal end of a patient's finger and connected with the HSAT unit to generate a peripheral arterial tone (PAT) signal. A band structure as described herein improves the accuracy of the generated signal. A non-limiting example finger probe is described in more detail in U.S. Pat. No. 6,916,289 to Schnall, assigned to the common assignee, the contents of which are hereby incorporated by reference.

Preventing veins in the measurement region, or in the surrounding tissues, from becoming distended with blood, even at very low pressures, is one advantage of a band structure as described. The physiological basis for this is that the veins are vastly more compliant than the arterial blood vessels, and become distended at pressures far below diastolic blood pressure. When veins do become distended, a local reflex known as the "veno-arteriolar reflex" occurs, and this results in the affected arteries constricting. This effect spreads to surrounding tissues over time. Therefore, it is advantageous to use a probe that covers all of the finger surface, especially including the fingertip, with enough pressure to stop the veins from becoming distended.

However, if sufficient pressure is applied around the wrist to cause the veins beyond it (i.e., further away from the heart) to fill up, all of the tissues from the wrist down to the fingertips can be affected by the induced reflex. If this happens, blood flow to the hand itself can be reduced. While the finger with a PAT probe might itself not suffer from venous distention, the arteries supplying blood to that finger can be affected. Also, the veno-arteriolar reflex spreads over time, so eventually even the finger within the PAT probe may also be affected. An uncontrolled level of force around the wrist from an overly tight wrist band could result in such venous pooling of the whole hand and, therefore, avoiding this situation is desirable. As the disclosed structure allows for substantial parts of the wrist perimeter surface not being directly in contact with the circumferential band, it allows for venous drainage.

Figure 3A:
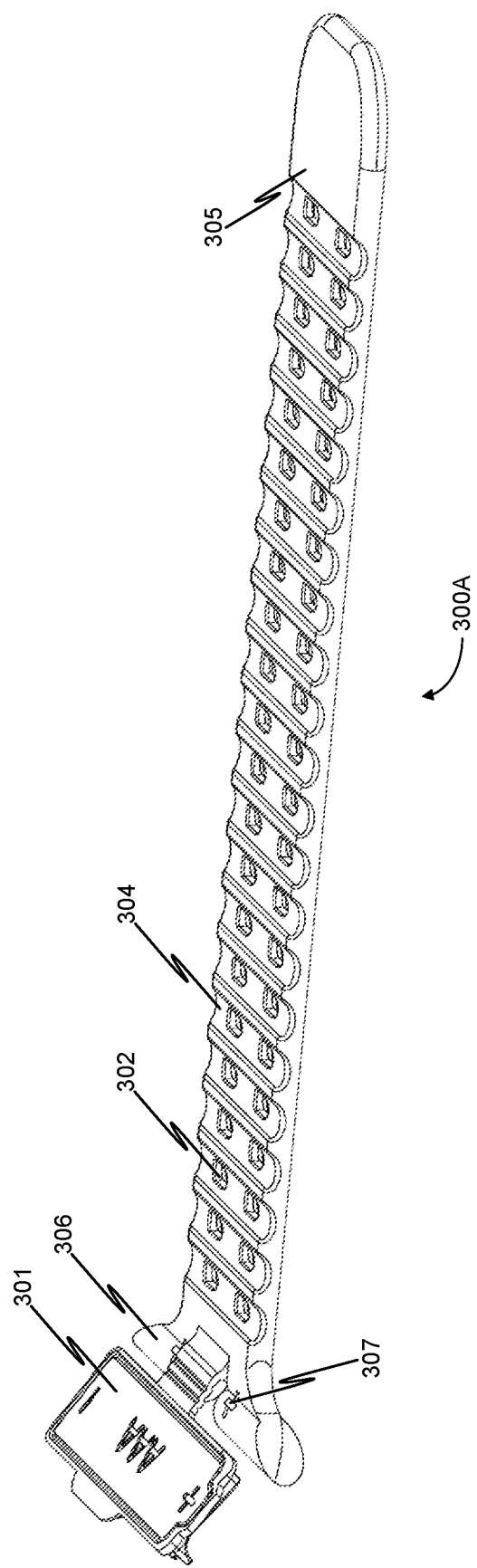
FIG. 3A is schematic illustration of an isometric top side view of a perforated band according to an embodiment.
Figure 3B:
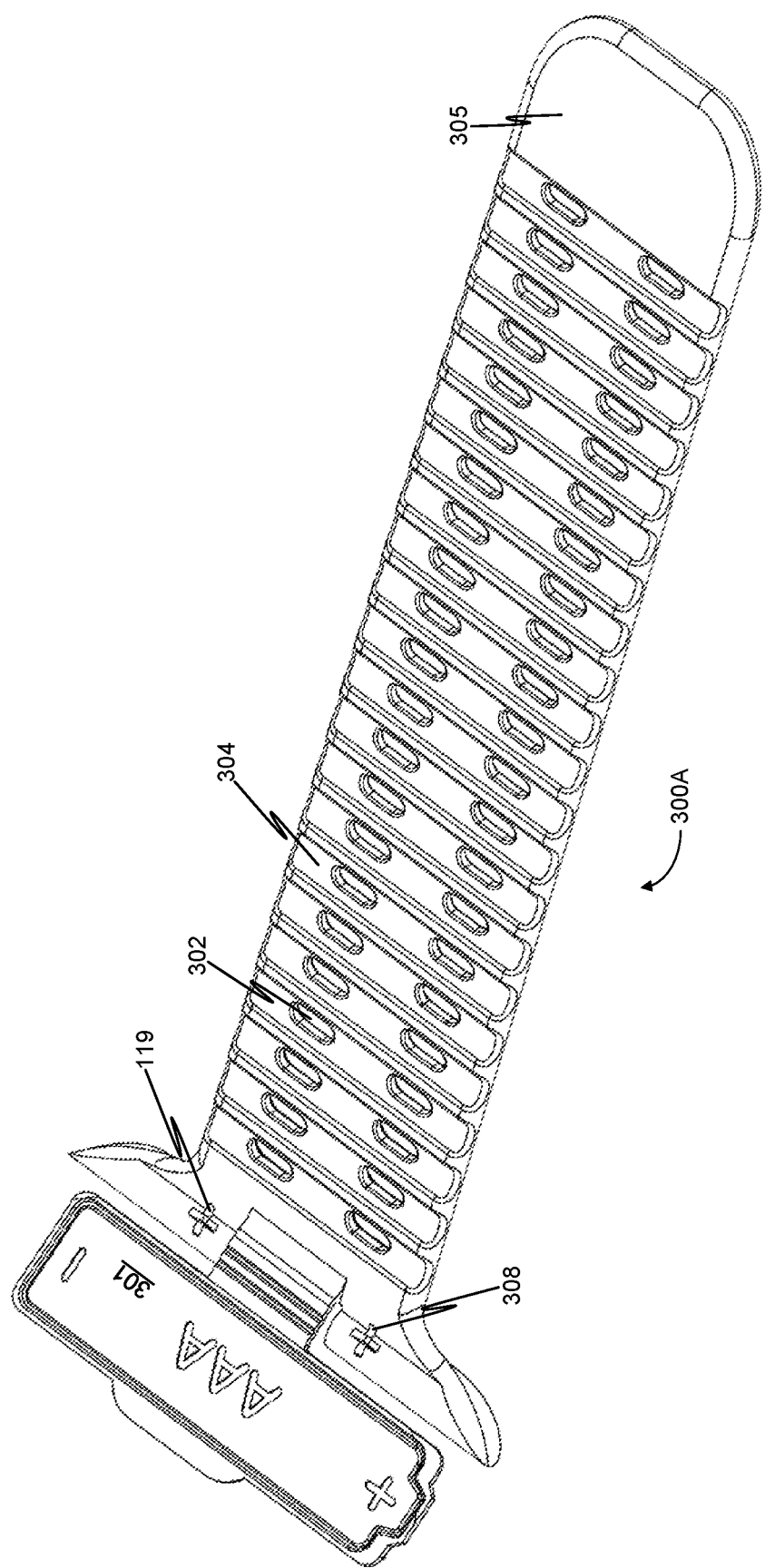
FIG. 3B is a schematic illustration of an isometric top view of a perforated band according to an embodiment.

FIG. 3A is a schematic illustration of an isometric top side view of a perforated band 300A and FIG. 3B is a schematic illustration of an isometric top view of the perforated band 300A according to an embodiment. The perforated band 300A includes a plurality of perforations (also known as adjustment holes) such as perforation 302. The adjustments holes are operative for receiving the pin 202 of the buckle clasp band 200A as the perforated band 300A is placed through the buckle 201. In this embodiment, the pin 202 includes two pins, and the perforated band 300A includes pairs of perforations adapted to accept the two pins. Once the perforated band 300A is fastened with the buckle 201 and pin 202, a remaining portion of the perforated band 300A may be placed through the guide 204 to secure the band 300A in place. The fastened bands 200A and 300A form together with the HSAT housing a loop which is positioned on an appendage of a human body.

In an embodiment the perforated band 300A includes a tapered distal end 305. The taper on the distal end allows for easier insertion through the buckle 201 and guide 204. The perforated band 300A may also include a plurality of ridges such as ridges 304. As with the buckle clasp band 200A, the ridges may serve to prevent occlusion of blood flow to and from the appendage and allow for a less rigid structure which is easier to fit around the human appendage.

The perforated band 300A also includes a wide member 306 which is adapted to fit into channel 127 (as shown in FIG. 1C). The wide member 306 includes a first perforation 307 and a second perforation 308. The member 306 is fitted into channel 127 of the bottom portion 100A so that first perforation 307 position is aligned with anchor point 104 and second perforation 308 is aligned with anchor point 103. When the two housing portions are assembled, cross pin 118 protrudes through the first perforation 307 and is held in position at anchor point 104, while cross pin 119 protrudes through the second perforation 308 and is held in position at anchor point 103.

A battery cover 301 may also be integrated into the perforated band 300A. In some embodiments, with proper adjustments, the battery cover 301 may be an integral part of the buckle clasp band 200A. A battery cover 301 which is an integral part may be preferable to a cover which is not integrated. For example, if a battery cover is manufactured from a separate piece of plastic (or other suitable material), this increases the number of parts required for assembly and may increase production complexity. Another deficiency is that a user can also lose such a part while preparing for an HSAT. By lowering the number of parts required, assembly is simpler, cheaper, and often faster. All these are qualities which are desirable, especially in a device which is intended as a disposable unit.

Figure 4:
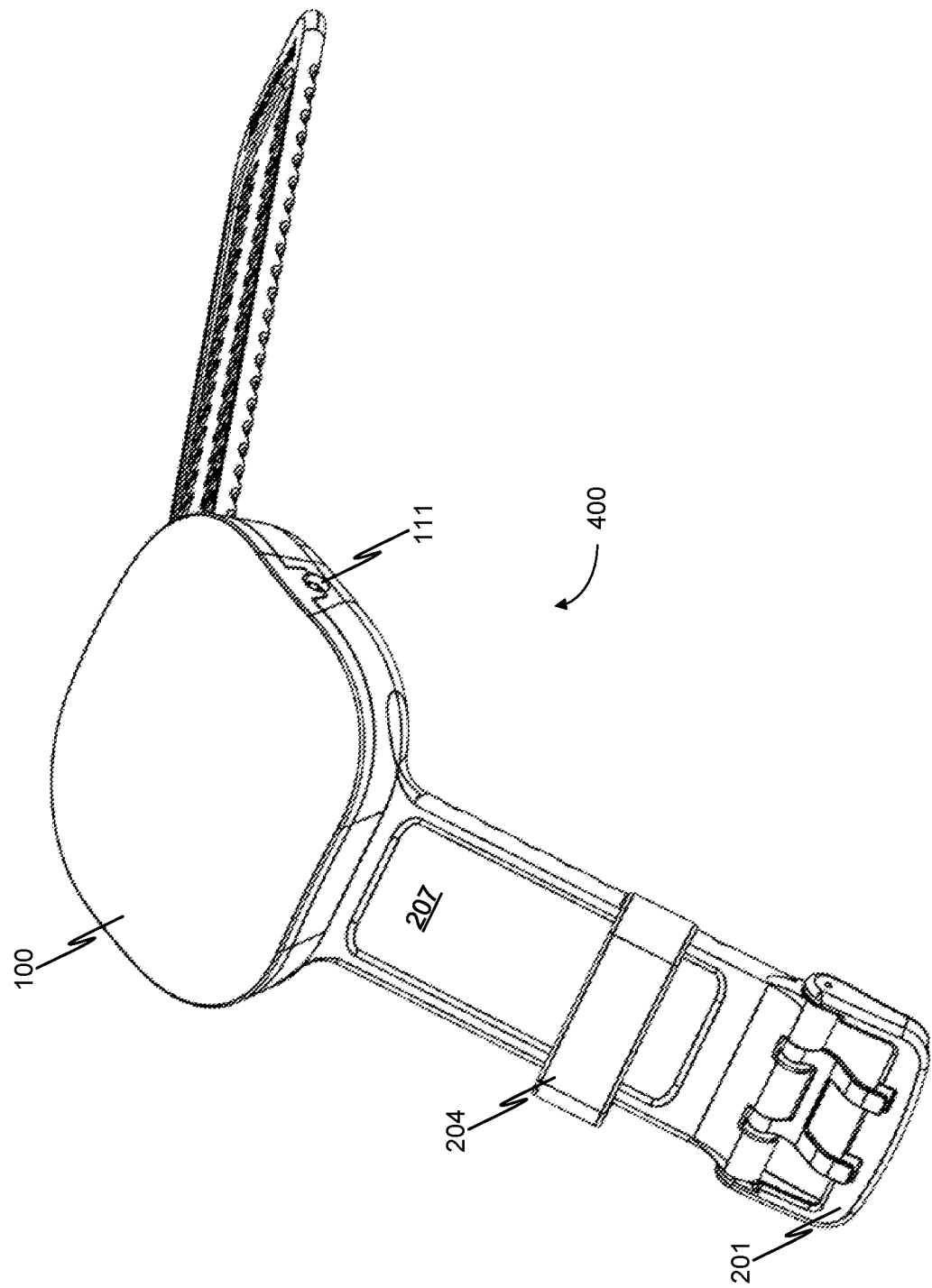
FIG. 4 is a schematic illustration of an isometric view of an assembled HSAT device housing and bands according to an embodiment.

FIG. 4 is a schematic illustration 400 of an isometric view of an assembled HSAT device housing 100 and bands according to an embodiment. The HSAT device housing 100 houses therein a control circuit board (such as a PCB, not shown in FIG. 4) which includes, for example, circuitry for controlling one or more sensors attached to the control circuit board, analog front-end circuit(s), memory device(s), transceiver(s), and one or more external sensors, such as a finger probe and a chest sensor. For example, the chest sensor may be communicatively connected to the control circuit with a cable (not shown) passed through opening 111 or, in other embodiments, be wirelessly connected to the control circuit board via a network interface controller (not shown). The control circuit, the chest sensor, or both, may include an accelerometer for measuring movements. In an embodiment, the HSAT device may be further connected to a tamper proof identification device such as, but not limited to, the device described in more detail in U.S. Pat. No. 8,485,448, assigned to the common assignee, the contents of which are incorporated by reference herein.

In an embodiment, the HSAT device housing 100 may have a substantially rectangular shape which may be defined by rounded edges. Rounding edges improves user experience, as a smooth surface is more pleasing to human touch. Rounded structures also have less stress and are therefore more resilient to damage.

Figure 5:
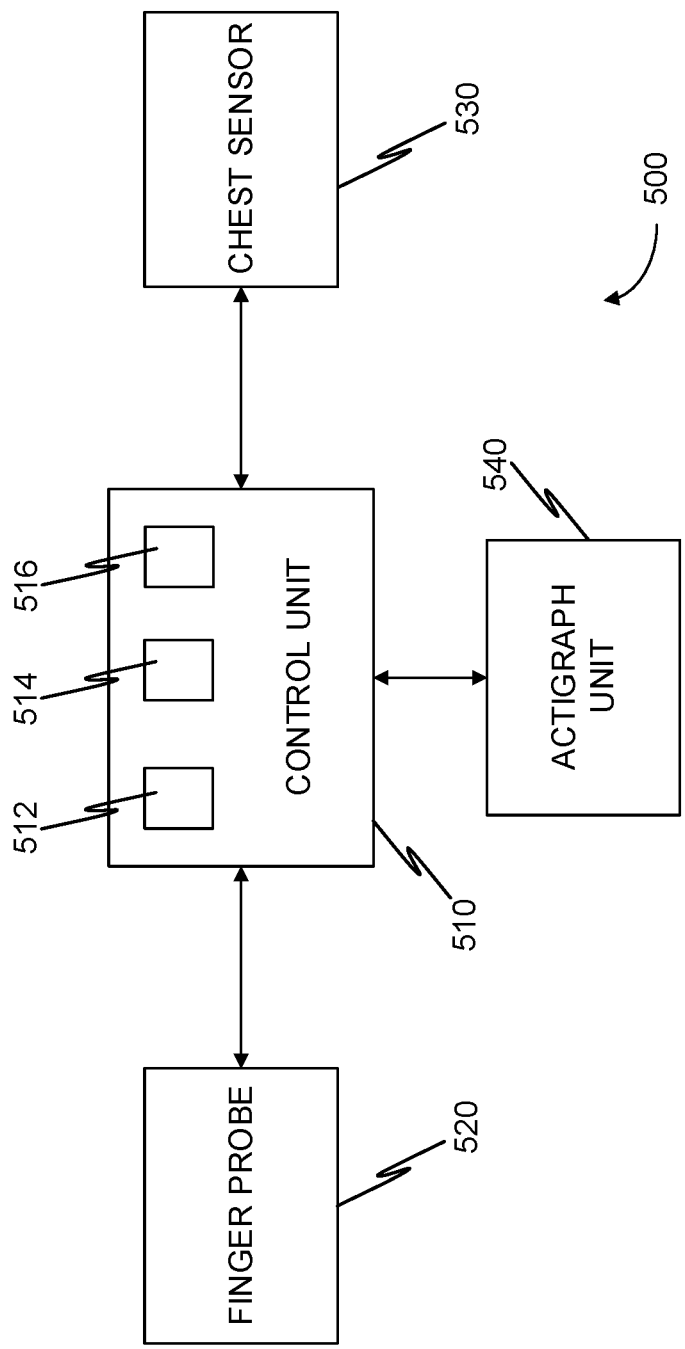
FIG. 5 is a schematic illustration of an HSAT unit according to an embodiment.

FIG. 5 is a schematic illustration of a HSAT unit 500 according to an embodiment. The HSAT unit 500 includes a control unit 510, which is communicatively connected to an actigraph unit 540, a finger probe 520, and a chest sensor 530. The control unit 510 may be implemented on a printed circuit board (not shown in FIG. 5), and may include components such as a processing circuitry 512, a memory 514, and a network interface controller (NIC) 516. In an embodiment, the NIC may be coupled with a transceiver (not shown), including an antenna, for transmitting and receiving wireless signals, for example to access a network or communicate with one or more sensors (such as a wireless chest sensor).

The processing circuitry 512 may be implemented with any combination of general-purpose microprocessors, microcontrollers, digital signal processors (DSPs), field programmable gate array (FPGAs), programmable logic devices (PLDs), System on Chip (SoC), controllers, state machines, gated logic, discrete hardware components, dedicated hardware finite state machines, or any other suitable entities that can perform calculations or other manipulations of information.

The processing circuitry 512 is coupled (e.g., via a bus) to the memory 514. The memory 514 may include a memory portion that contains instructions that when executed by the processor performs the method described in more detail herein. The memory 514 may be further used as a working scratch pad for the processor, a temporary storage, and others, as the case may be. The memory 514 may be a volatile memory such as, but not limited to random access memory (RAM), or non-volatile memory (NVM), such as, but not limited to, Flash memory. Memory 514 may further include memory portion containing measurements generated by any of a finger probe, an actigraph unit, and a chest sensor. The memory 514 may further include a unique identifier of the unit 500. The unique identifier may be, for example, a MAC address, serial number, device ID, a combination thereof, and the like.

In an embodiment, the memory 514 may further be used as a buffer to store data generated by one or more sensors communicatively coupled thereto. In some embodiments, the memory may store one or more parameters associated with a pulse oximeter connected thereto. A pulse oximeter may be utilized as part of a finger probe. The pulse oximeter includes a light emitter and photodetector. As each light emitter and photodetector pair operate in a non-identical way to other pairs, operating parameters may be stored in the memory and used to rectify inaccuracies stemming from the difference of real world devices to theoretical model. For example, an LED may have a theoretical wavelength value of 540 nanometers (corresponding to 'green' light). However, not every manufactured LED will transmit this exact wavelength. Some may be 542 nm, some may be 538 nm, etc. By detecting the exact wavelength and storing this wavelength value into the memory 514, the processing circuitry 512 may be used to compensate the received measurement from the oximeter, taking into account the discrepancy between the real world value and the theoretical model.

The processing circuitry 512 is further coupled to a NIC 516. The NIC 516 is configured to communicatively connect the control unit 510 to a network (discussed in more detail in FIG. 6 below) or other device using a wireless network connection. In an embodiment, the NIC 516 may control a plurality of network interfaces (not shown). A network interface may include, for example, a short range wireless transceiver, operating a network protocol such as Bluetooth® or Wi-Fi®. In an embodiment the NIC 516 communicatively connects the unit 500 to a user device, which in turn may be connected to a network.

The processing circuitry 512, the memory 514, or both may store include machine-readable media for storing software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the one or more processors, cause the processing circuitry 512 to perform the various functions described in further detail herein. In some embodiments the software may be downloaded over a network to the device. This allows for updating the device with the latest available software.

The finger probe 520 may be, for example, an oximeter. In an embodiment, the finger probe 520 includes a light source (such as a light emitting diode), a photosensor, and a static pressure field applicator which applies a static pressure field at the site of measurement. An example of such a probe is discussed in more detail in U.S. Pat. No. 7,621,877, assigned to the common assignee, the contents of which are hereby incorporated by reference.

The control unit 510 may be further connected to a power source (not shown) such as, but not limited to, a battery. The control unit 510 may be connected to the chest sensor 530 via one or more wires for data transmission and power supply. The chest sensor 530 may include an accelerometer (not shown), so that when the chest sensor 530 is applied to the chest of a human patient (for example, by using an adhesive), the accelerometer generates measurements which may be translated to movements of the torso. The chest sensor 530 may be self-powered and connected to the control unit by wireless communication. In another embodiment, a wireless chest sensor (not shown) may be communicatively connected to a user device which is communicatively connected to the HSAT unit 500.

The actigraph unit 540 may be communicatively connected to the control unit 510. In an embodiment, the actigraph unit 540 and control unit 510 may be integrated into a single electronic circuit. The actigraph unit 540 includes one or more accelerometers (not shown), which in some embodiments are connected to a low pass filter to ignore external vibrations (i.e., noise). The actigraph unit 540 may either include, or be connected to, a clock circuit (not shown) to generate measurements at specific time intervals.

Figure 6:
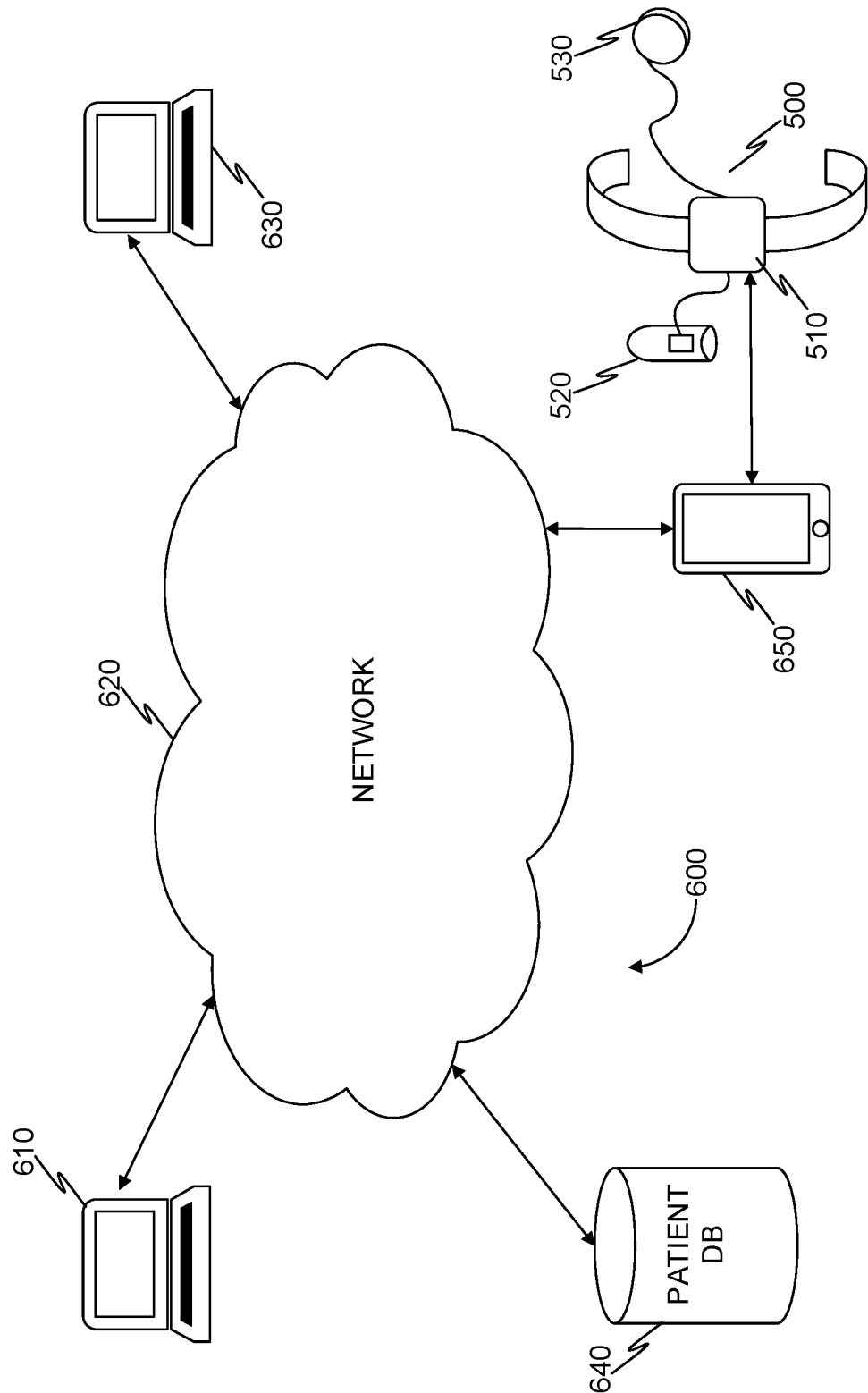
FIG. 6 is a network diagram utilized to describe various disclosed embodiments.

FIG. 6 is a network diagram 600 utilized to describe various disclosed embodiments. An administrator device 610 is communicatively connected to a network 620.

In an embodiment, the network 620 may be configured to provide connectivity of various sorts, as may be necessary. The network 620 may be, but is not limited to, a wireless, cellular or wired network, a local area network (LAN), a wide area network (WAN), a metro area network (MAN), the Internet, the worldwide web (WWW), similar networks, a combination thereof, and the like. In some embodiments, the network 620 may further include a cloud based computing environment. In such embodiments, any of the manufacturer device 630, patient database 640, and administrator device 610 may be implemented as components of the cloud based computing environment. In such cases the devices may be implemented for example as virtual machines.

The network 620 further provides connectivity for a manufacturer device 630 and a patient database (DB) 640. In some embodiments, the network 620 may provide connectivity to a user device 650, an HSAT unit 500, or both. In some embodiments, the HSAT unit 500 may connect to the network 620 through the user device 650.

In an embodiment, each of the administrator device 610, the client device 650, and the manufacturer device 630 may be any one of: personal computing device, laptop, desktop, mobile phone, smartphone, tablet, and the like.

A manufacturer device 630 may be configured to embed the HSAT unit 500 with a unique identifier such as, but not limited to, a MAC address, serial number, device ID, a combination thereof, and the like. In some embodiments, any of the control unit 510, the finger probe 520, and the chest sensor may be embedded with a unique identifier.

The administrator device 610 may be configured to assign a specific (i.e., unique) HSAT unit to a patient. The patient is associated with a user device (such as the user device 650), an electronic account, or both. Association may be achieved by storing patient identifying information and other information, for example, in a patient database 640. The administrator device 610 may send an instruction to the patient database 640 to update a table containing therein a patient identifier to be associated with a unique HSAT unit identifier.

Prior to activation (i.e., after powering on but before administering a test) of the HSAT unit 500, the unit 500 may require that credentials be supplied. For example, the HSAT unit 500 may be communicatively connected to a user device 650. The user device 650 receives a key as an input (for example, through an I/O interface of the user device 650) and the unique identifier of the HSAT unit 500. The input and unique identifier are transmitted over the network to the administrator device 610. The administrator device 610 may perform a check using the patient database 640 to determine whether the patient identifying information and the unique identifier match the database record. If so, the administrator unit 610 may send an instruction to the HSAT unit 500 to activate; otherwise, the unit will not activate.

In an embodiment, the key may be a passcode, personal identification number, or other unique key, which may be generated by, for example, the administrator device 610. By using such a key, no information is sent over a network which may be used by a third party intercepting such information, to identify a patient. This is advantageous for complying with, for example, various privacy laws.

Figure 7:
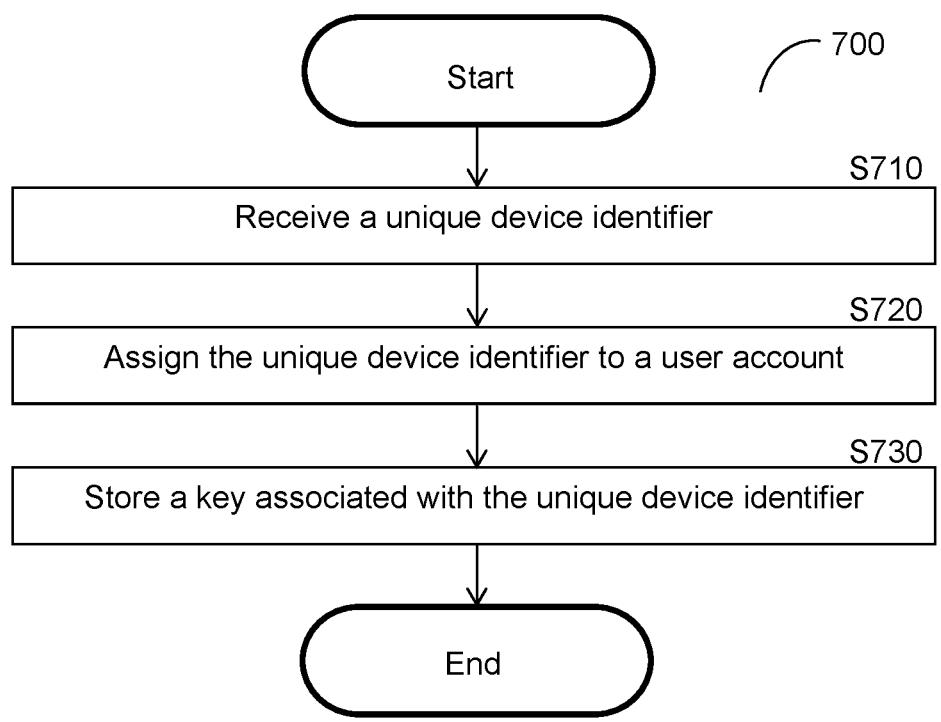
FIG. 7 is a is a flowchart of a method for assigning an HSAT unit to a user account of a patient according to an embodiment.

FIG. 7 is a flowchart of a method for assigning an HSAT unit to a user account of a patient according to an embodiment. In an embodiment, the method may be performed by the administrator device 610, FIG. 6.

At S710, a unique device identifier (ID) is received. The unique device ID may be embedded, for example, as code stored in a memory, such as a read only memory, of an HSAT unit. An administrator device may receive one or more unique device identifiers and store the identifier(s) in a memory or storage of the administrator device, or other device accessible to the administrator device. The unique device ID may be received from a manufacturer device.

At S720, the unique device ID is assigned to a user account. In an embodiment, assigning the unique device ID includes accessing a table of a patient database (e.g., the patient database 640, FIG. 6) which includes a unique patient identifier, and updating a row in the table so that a user account associated with a particular row is in the same row as the assigned unique device ID.

At S730, a key is generated and stored with the unique device ID. In an embodiment, the association (performed, for example, by updating a table including a column of unique device IDs and a column of corresponding keys) is performed by the administrator device 610. In some embodiments, the table is accessible by the manufacturer device 630, and activation as described below may be performed with the manufacturer device 630. In such embodiments, no patient identifiable information is stored on the table accessible to the manufacturer device 630.

Figure 8:
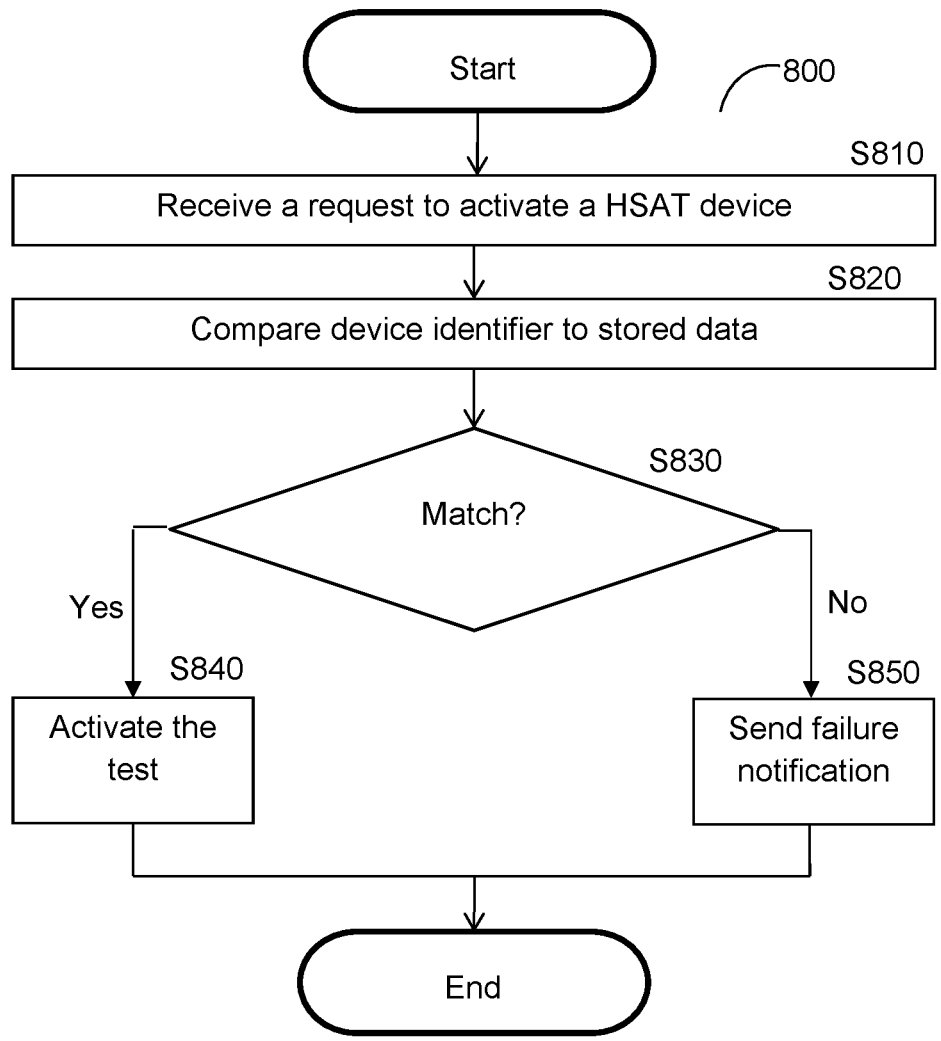
FIG. 8 is a flowchart of a method for activating an HSAT unit according to an embodiment.

FIG. 8 is a flowchart of a method for activating a HSAT unit according to an embodiment. In an embodiment, the method may be performed by the manufacturer device 630, FIG. 6.

In some embodiments it may be advantageous to require activation prior to beginning an HSAT. For example, a provider may wish to activate the test only during certain hours, or only activate the test for a user who is authorized to perform the test. Since the test may be administered without an attending professional, it may be desirable to add a confidence level requirement in order to ensure that the person connected to the device is indeed the intended patient, and that the test is being performed as the physician intended it to.

At S810, a request to activate the HSAT device is received. The request may include a unique device ID which is read from a memory of the device and a passcode (or key). In an embodiment, the passcode may be provided as an input from a user of a user device which is communicatively connected to the HSAT device (e.g., the user device 650 which is communicatively connected to the HSAT device 500, FIG. 6).

At S820, data related to the received unique device ID is compared to stored data for the HSAT device. In an embodiment, S820 includes comparing the device identifier of the HSAT device to stored data (e.g., unique device identifier associated with a given key as discussed further above with respect to FIG. 7). In a further embodiment, S820 may also include comparing the passcode or key to stored data. This may include performing a lookup on a table (such as described in FIG. 7 above) to determine if the unique device ID appears in the table.

At S830, it is determined if the comparison yielded a match such that the unique device ID is valid and, if so, execution continues at S840; otherwise, execution continues at S850.

At S840, when the comparison yields a match, an instruction is sent to the HSAT unit to activate the test. Activating the test may include, but is not limited to, powering on one or more sensors, transmitting data from the one or more sensors, or any combination thereof.

At S850, when the comparison yields a mismatch, a notification that the activation failed is sent to the user device communicatively coupled with the HSAT unit. In an embodiment, the notification may include an input field to receive another pair of unique device ID and key. In some embodiments (not shown), when the notification includes an input field to receive another key, the process may redirect to S820. In other embodiments (shown), execution may end after S850.

Figure 9:
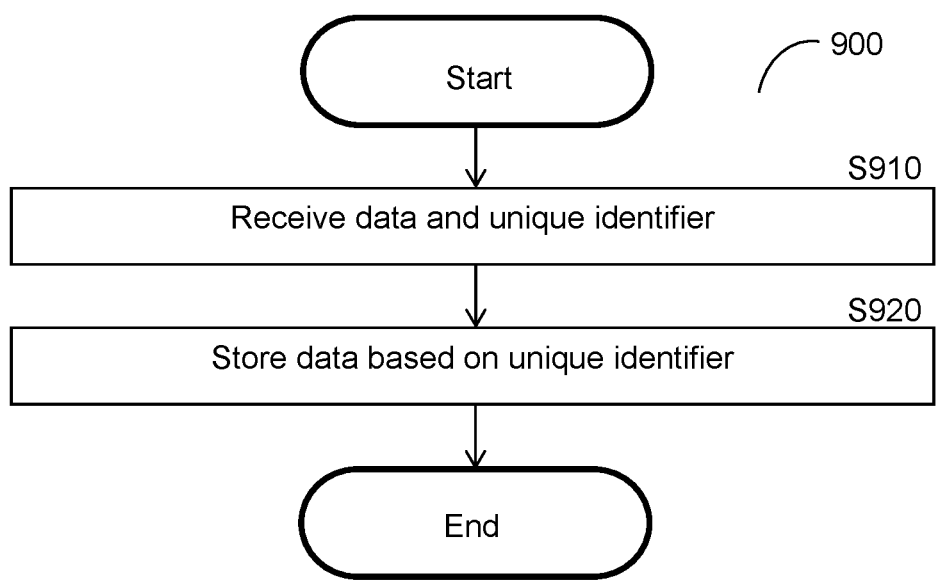
FIG. 9 is a flowchart of a method for receiving confidential patient information from an HSAT unit in compliance with privacy regulations according to an embodiment.

FIG. 9 is a flowchart illustrating a method for receiving data containing confidential patient information from an HSAT unit in compliance with privacy regulations according to an embodiment. In an embodiment, the method may be performed by the administrator device, FIG. 6.

As there are numerous rules and regulations concerning medical data, it may be desirable to have a system in place which is able to comply with as many such regulations as possible, especially concerning transfer of patient information over a network. More specifically, it is desirable to have a system which can securely transmit data, thereby ensuring that the information indicated therein remains confidential.

At S910, data to be stored is received (for example, from the manufacturer device 630, FIG. 6). In an embodiment, the HSAT data may be associated with a unique ID. For example, each packet of data generated from the HSAT data may include the unique ID. HSAT data may be generated from the one or more sensors of an HSAT unit.

The manufacturer device does not have access to the patient information and may therefore direct the data to be stored any location to which the administrator device directs. For example, the administrator device may configure the user device to store data received from an HSAT unit having a specific identifier at a predetermined storage site. Configuring the user device to store HSAT data may include sending to the user device an address of a network accessible storage, such as a secure file transfer protocol (SFTP) server.

At S920, the received data is stored in a predetermined storage based on the received unique ID. For example, a table may be generated including a column of unique IDs and a column of designated storage sites. A designated storage site may be, but is not limited to, an address of a network accessible storage device. An administrator device may access the data by reading it from the designated storage site. The administrator device may match the designated storage site with the unique device ID and patient information. Therefore, in an embodiment, the only device capable of matching patient information with the generated medical information is the administrator device.

Upon activation (e.g., as described with respect to FIG. 8 above), the HSAT unit begins to generate data. The data is transmitted over a network to a predesignated storage site. In an embodiment, the HSAT unit may request from a manufacturer device a location in which to write the data generated by the sensors of the HSAT unit. The manufacturer device may respond with instructions for storing the data on the predetermined storage device (or site). In an embodiment, the predetermined storage device may be selected by the administrator device.

By isolating the information accessible to each device, it is ensured that only the device of the medical professional (i.e., the administrator device) has access to the generated data from the HSAT unit and to the corresponding patient identifier. The manufacturer is able to provide the medical professional with a system which handles the gathering and storage of information, but since no identifiable information is accessible to the manufacturer, the data is more secure, and therefore may be compliant with privacy regulations.

Figure 10:
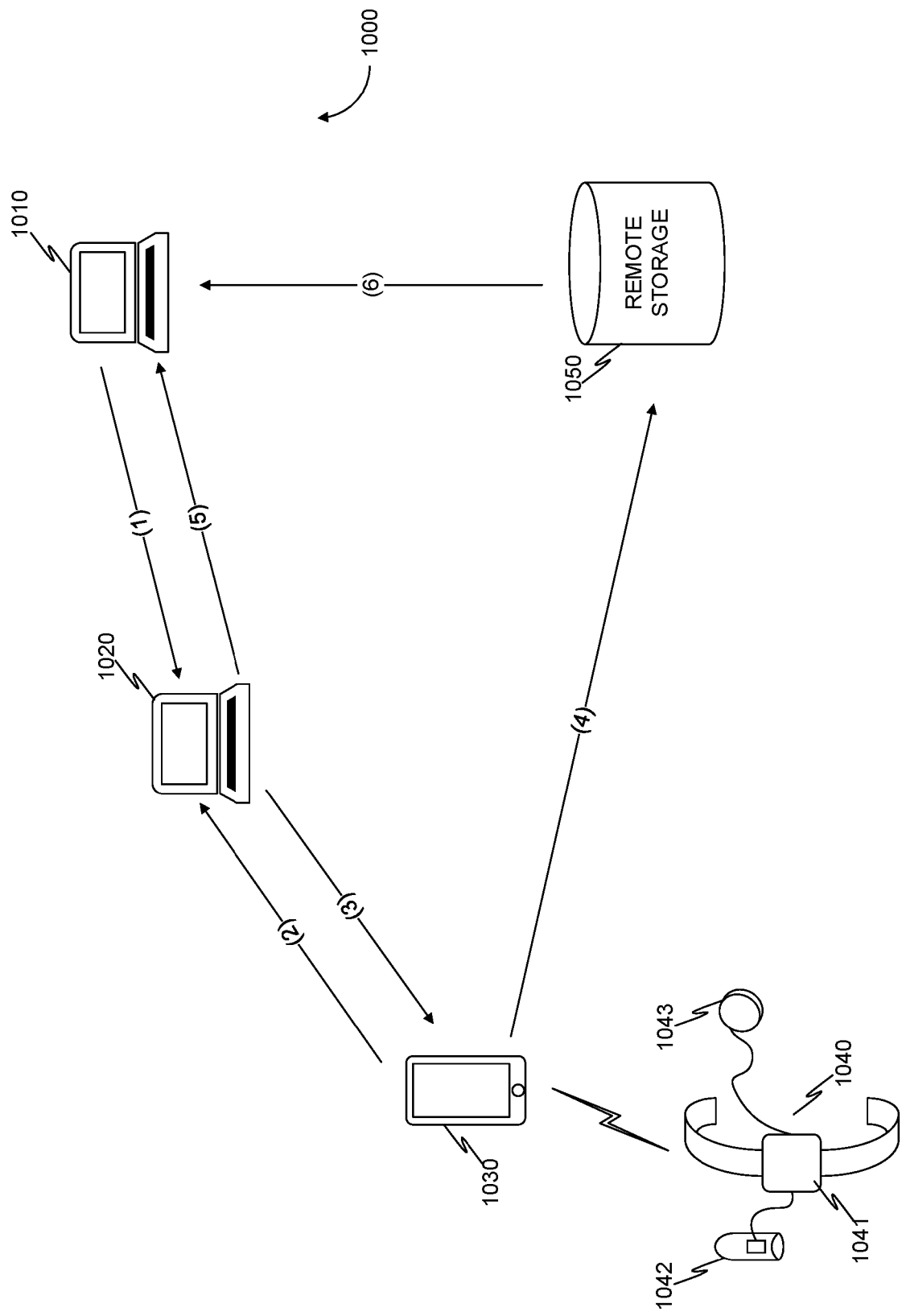
FIG. 10 is a schematic illustration utilized to demonstrate assigning, activating, and receiving data from an HSAT unit.

FIG. 10 is a schematic illustration utilized to demonstrate assigning, activating, and receiving data from an HSAT unit. A computer server 1010 performs registration (1) of an HSAT unit 1040 with a device server 1020. In an embodiment, the computer server 1010 is associated with a healthcare provider. The healthcare provider may operate a plurality of devices such as, but not limited to, the administrator device (not shown) discussed in more detail above. The administrator device may, for example, instruct the computer server 1010 to perform HSAT registration. In an embodiment, registration of an HSAT unit may include associating a unique ID (such as a serial number) together with a key (such as a 4 digit personal identification number code) and a user account of a healthcare provider (such as a doctor's email address).

The HSAT unit 1040 is communicatively connected to a user device 1030. Upon activation of the test, the user device may transmit (2) over a network a request to initiate the test. The request may include, for example, the unique ID and the key. In an embodiment, the request is transmitted to the device server 1020. In an embodiment, the device server 1020 may be the manufacturer device 630 discussed in more detail above.

The device server 1020 performs authentication of the request, for example by comparing a received unique ID and key with a table of stored unique ID and key pairs. An example of such an authentication is described further above with respect to FIG. 8. If the request is successfully authenticated, the device server sends (3) the user device 1030 a network address of a remote storage 1050 to which the user device 1030 should transmit medical information generated by the HSAT unit 1040.

During the test phase, the HSAT unit 1040 generates measurements from sensors. Sensors may include one or more: of chest sensors 1043, an actigraph of a control unit 1041, and a finger probe 1042, all of which are described further herein above.

The measurements are transmitted to the user device 1030 which is communicatively connected to a remote storage 1050. The user device 1030 uploads (4) the measurements to the remote storage 1050. In an embodiment, the uploaded measurements may include the unique ID of the HSAT unit 1040 and a timestamp.

The device server 1020 further sends (5) the network address of the remote storage and unique ID to the computer server 1010. The computer server 1010 can then request measurements associated with a unique ID by providing the unique ID from the remote storage 1050, and the measurements may be provided (6) to the computer server 1010.

In some embodiments, the device server 1020 may provide to the user device 1030 a network address of a remote storage and a storage address (e.g., a folder) in which to store the generated measurements. The network address and storage address may then be provided to the computer server 1010. The computer server may request measurements from the remote storage by providing the storage address, either in place of, or in addition to, the unique ID.

Figure 11:
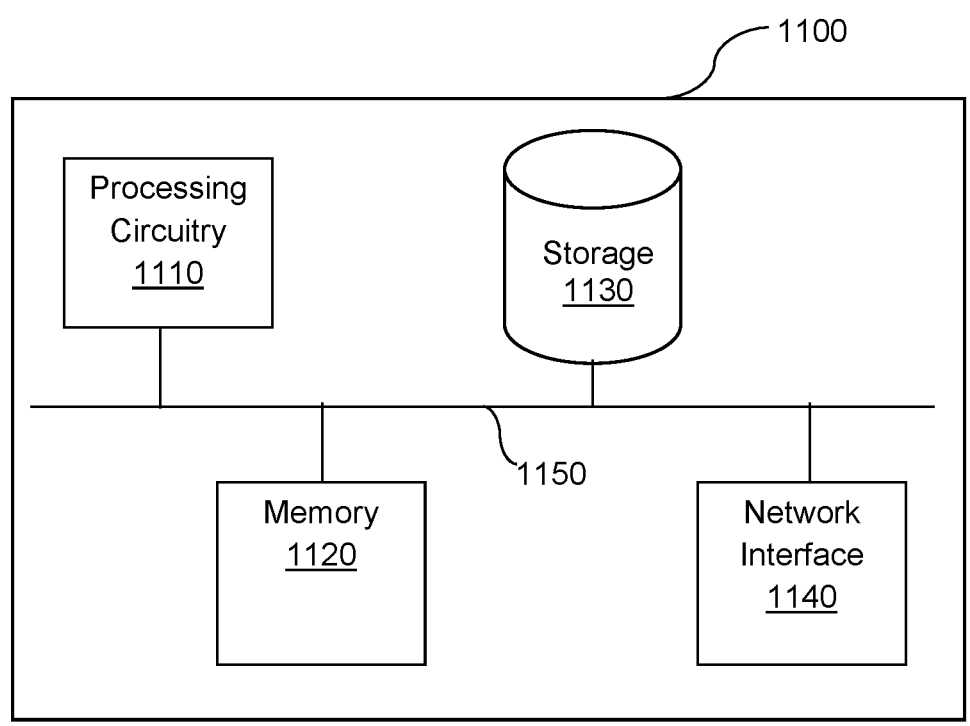
FIG. 11 is a schematic diagram of a device which may be configured to perform at least a portion of the disclosed embodiments.

FIG. 11 is an example schematic diagram of a device 1100 which may be configured to perform at least a portion of the disclosed embodiments. The device 1100 includes a processing circuitry 1110 coupled to a memory 1120, a storage 1130, and a network interface 1140. In an embodiment, the components of the device 1100 may be communicatively connected via a bus 1150.

The processing circuitry 1110 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), graphics processing units (GPUs), tensor processing units (TPUs), general-purpose microprocessors, microcontrollers, digital signal processors (DSPs), and the like, or any other hardware logic components that can perform calculations or other manipulations of information.

The memory 1120 may be volatile (e.g., random access memory, etc.), non-volatile (e.g., read only memory, flash memory, etc.), or a combination thereof.

In one configuration, software for implementing one or more embodiments disclosed herein may be stored in the storage 1130. In another configuration, the memory 1120 is configured to store such software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry 1110, cause the processing circuitry 1110 to perform the various processes described herein.

The storage 1130 may be magnetic storage, optical storage, and the like, and may be realized, for example, as flash memory or other memory technology, compact disk-read only memory (CD-ROM), Digital Versatile Disks (DVDs), or any other medium which can be used to store the desired information.

The network interface 1140 allows the device 1100 to communicate for purposes such as, but not limited to, receiving unique device identifiers and/or keys, storing data, both, and the like.

It should be understood that the embodiments described herein are not limited to the specific architecture illustrated in FIG. 11, and other architectures may be equally used without departing from the scope of the disclosed embodiments.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A method for securely transferring medical data for a sleep test, comprising:
   receiving, at a manufacturer device, a patient key associated with a wearable sleep test device from a healthcare administrator device,
   the wearable sleep test device having an embedded unique identifier and comprising at least two sensors comprising a finger probe and a chest sensor,
   capturing, by the at least two sensors of the wearable sleep test device, the medical data during the sleep test by:
      generating, by the finger probe, a signal from a finger of a patient, and
      generating, by the chest sensor, one or more measurements of movement of a torso of the patient;
   receiving, at the manufacturer device, a request to store the medical data captured by the at least two sensors, the medical data comprising the signal generated by the finger probe and the one or more measurements of movement of the torso generated by the chest sensor, from the wearable sleep test device;
   configuring the wearable sleep test device to store the medical data in at least one designated storage location, wherein each of the at least one designated storage location is accessible to the wearable sleep test device and to the healthcare administrator device;
   storing, by the wearable sleep test device, the medical data in the at least one designated storage location; and
   sending, by the manufacturer device, the at least one designated storage location and the embedded unique identifier to the healthcare administrator device.

2. The method of claim 1, wherein configuring the wearable sleep test device to store the medical data further comprises:
   sending, to the wearable sleep test device, instructions, a network address, and a location of a storage device at the network address, wherein the instructions are for sending the medical data to the storage device at the network address.

3. The method of claim 1, wherein the at least one designated storage location is a plurality of storage locations, wherein configuring the wearable sleep test device to store the medical data further comprises:
   sending, to the wearable sleep test device, instructions for storing an identical copy of at least a portion of the medical data at each of the plurality of storage locations.

4. The method of claim 1, wherein the at least one designated storage location is a plurality of storage locations, wherein configuring the wearable sleep test device to store the medical data further comprises:
   sending, to the wearable sleep test device, instructions for storing a first portion of the medical data at a first storage location of the plurality of storage locations and for storing a second portion of the medical data at a second storage location of the plurality of storage locations.

5. The method of claim 4, wherein the first portion of the medical data includes data captured by a first sensor of the at least two sensors, wherein the second portion of the medical data includes data captured by a second sensor of the at least two sensors.

6. The method of claim 1, wherein the manufacturer device is a device server.

7. A non-transitory computer readable medium having stored thereon instructions for causing a processing circuitry to execute a process for securely transferring medical data for a sleep test, the process comprising:
- receiving, at a manufacturer device, a patient key associated with a wearable sleep test device from a healthcare administrator device, the wearable sleep test device having an embedded unique identifier and comprising at least two sensors comprising a finger probe and a chest sensor;
- capturing, by the at least two sensors of the wearable sleep test device, the medical data during the sleep test by:
  - generating, by the finger probe, a signal from a finger of a patient, and
  - generating, by the chest sensor, one or more measurements of movement of a torso of the patient;
- receiving, at the manufacturer device, a request to store the medical data captured by the at least two sensors, the medical data comprising the signal generated by the finger probe and the one or more measurements of movement of the torso generated by the chest sensor, from the wearable sleep test device;
- configuring the wearable sleep test device to store the medical data in at least one designated storage location, wherein each of the at least one designated storage location is accessible to the wearable sleep test device and to the healthcare administrator device;
- storing, by the wearable sleep test device, the medical data in the at least one designated storage location; and
- sending, by the manufacturer device, the at least one designated storage location and the embedded unique identifier to the healthcare administrator device.

8. The non-transitory computer readable medium of claim 7, wherein the process comprises:
- sending, to the wearable sleep test device, instructions, a network address, and a location of a storage device at the network address, wherein the instructions are for sending the medical data to the storage device at the network address.

9. The non-transitory computer readable medium of claim 7, wherein the at least one designated storage location is a plurality of storage locations, wherein the process comprises:
- sending, to the wearable sleep test device, instructions for storing an identical copy of at least a portion of the medical data at each of the plurality of storage locations.

10. The non-transitory computer readable medium of claim 7, wherein the at least one designated storage location is a plurality of storage locations, wherein the process comprises:
- sending, to the wearable sleep test device, instructions for storing a first portion of the medical data at a first storage location of the plurality of storage locations and for storing a second portion of the medical data at a second storage location of the plurality of storage locations.

11. The non-transitory computer readable medium of claim 10, wherein the first portion of the medical data includes data captured by a first sensor of the at least two sensors, wherein the second portion of the medical data includes data captured by a second sensor of the at least two sensors.

12. The non-transitory computer readable medium of claim 7, wherein the wearable sleep test device comprises a sleep apnea testing device.

13. The non-transitory computer readable medium of claim 7, wherein the manufacturer device is a device server.

* * * * *